United States Patent [19]

Gomm

[11] 4,003,898
[45] Jan. 18, 1977

[54] PROCESS FOR THE MANUFACTURE OF CATIONIC DYESTUFFS
[75] Inventor: Walter Gomm, Cologne, Germany
[73] Assignee: Bayer Aktiengesellschaft, Leverkusen, Germany
[22] Filed: Feb. 26, 1971
[21] Appl. No.: 119,393
[30] Foreign Application Priority Data
  Mar. 6, 1970  Germany ........................ 2010579
[52] U.S. Cl. .................... 260/247.1 L; 8/1 D; 260/247.2 B; 260/247.5 FP; 260/283 CN; 260/283 S; 260/287 T; 260/287 P; 260/288 CE; 260/288 CF; 260/326.27; 260/376.5 SF; 260/326.5 B; 260/326.62; 260/326.9
[51] Int. Cl.² .......... C07D 209/90; C07D 413/06; C07D 401/06; C07D 401/10
[58] Field of Search ... 260/326.9, 288 CE, 288 CF, 260/293.61, 247.2 B, 247.5 FP, 247.1 L, 283 S, 287 T, 326.27, 326.55 F, 326.5 B, 326.62, 283 CN, 287 P

[56] References Cited
UNITED STATES PATENTS 3,347,865  10/1967  Brack et al. .................. 260/313.1
3,853,913  12/1974  Brack et al. .................. 260/326.9
3,959,310  5/1976   Brack et al. .................. 260/326.9

Primary Examiner—Donald G. Daus
Assistant Examiner—Mary C. Vaughn
Attorney, Agent, or Firm—Plumley and Tyner

[57] ABSTRACT

Process for the manufacture of dyestuffs of the general formula

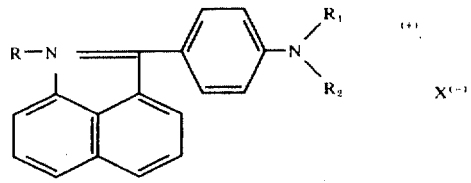

wherein R, $R_1$, $R_2$ represent an alkyl, cycloalkyl, aralkyl or aryl radical or R is alkyl bonded to the naphthalene ring or $R_1$ is alkyl bonded to $R_2$ or bonded to the adjacent six-membered ring and X stands for an anion by condensation of naphtholactames with aromatic amines with the addition of phosphorus pentoxide.

6 Claims, No Drawings

PROCESS FOR THE MANUFACTURE OF CATIONIC DYESTUFFS

The subject of the present invention is a process for the manufacture of cationic dyestuffs of general formula

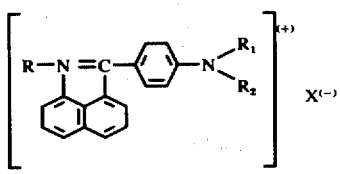

wherein
R represents an alkyl, cycloalkyl, aralkyl or aryl radical or an alkyl radical being connected with the naphthalenering in adjacent position to the nitrogen atom,
$R_1$ represents an alkyl, cycloalkyl, aralkyl or aryl radical,
$R_2$ represents an alkyl, cycloalkyl or aralkyl radical or $R_1$ and $R_2$ are alkyl radicals being connected with each other or $R_1$ or $R_2$ are alkyl radicals being connected with the carbon atom of the phenyl ring in the adjacent position to the nitrogen atom.
X represents an anion,
and wherein the rings and the acyclic radicals are unsubstituted or contain non-ionic substituents, by condensation of a compound of general formula

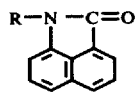

wherein
R has the indicated meaning, with an aromatic amine of formula

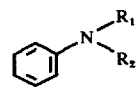

wherein
$R_1$ and $R_2$ have the indicated meaning
and the benzene ring of the amine component is unsubstituted or contains non-ionic substituents, with the proviso that the p-position relative to the nitrogen must be unsubstituted, using an inorganic acid halide as the condensation agent, and wherein the condensation is carried out with the addition of phosphorus pentoxide.

Suitable non-ionic substituents are, for example, alkyl, alkoxy, acyloxy, aryloxy, alkylmercapto, arylmercapto, amino, acylamino, alkylamino, aralkylamino, acyl, alkoxycarbonyl, amidocarbonyl and nitrile groups, as well as halogen atoms.

Possible radicals R are especially: alkyl radicals, such as methyl, ethyl, n-propyl, iso-propyl, n-butyl, isobutyl, iso-amyl, n-pentyl and n-hexyl as well as their alkoxy derivatives, such as methoxymethyl, ethoxymethyl, methoxyethyl and ethoxyethyl, their alkoxycarbonyl derivatives, such as methoxycarbonylmethyl, ethoxycarbonylmethyl, methoxycarbonylethyl and alkoxycarbonylethyl, their amindocarbonyl derivatives, such as dimethylamidocarbonylmethyl, diethylamidocarbonylmethyl, dimethylamidocarbonylethyl and diethylamidocarbonylethyl, $\beta$-piperidinylethyl and $\beta$-morpholinylethyl, their halogen derivatives, such as $\beta$-chloroethyl, their nitrile derivatives, such as $\beta$-cyanethyl, their amine derivatives, such as $\beta$-dimethylaminoethyl and $\beta$-diethylaminoethyl, cycloalkyl radicals, such as cyclohexyl, aralkyl radicals, such as benzyl and $\beta$-phenylethyl, and aryl radicals, such as unsubstituted phenyl and substituted phenyl, preferably alkylphenyl, such as 4-methylphenyl or alkoxyphenyl, such as 4-methoxyphenyl.

Preferred alkyl radicals $R_1$ are, for example: methyl, ethyl, n-propyl, iso-propyl, n-butyl, iso-butyl and iso-amyl as well as their halogen derivatives, such as $\beta$chloroethyl, their nitrile derivatives, such as $\beta$-cyanethyl, and their alkoxycarbonyl derivatives, such as methoxycarbonylmethyl, ethoxycarbonylmethyl, methoxycarbonylethyl and ethoxycarbonylethyl.

Cycloalky radicals $R_1$ are for example: cyclohexyl.

Aralkyl radicals $R_1$ are for example: benzyl.

Aryl radicals $R_1$ are for example: unsubstituted phenyl and substituted phenyl, preferably alkylphenyl, such as 4-methylphenyl, alkoxyphenyl, such as 4-methoxyphenyl and 4-ethoxyphenyl, and halogenophenyl, such as 4-chlorophenyl.

Particularly suitable alkyl radicals $R_2$ are for example: methyl, ethyl, n-propyl, iso-propyl, n-butyl, isobutyl and iso-amyl, as well as their halogen derivatives, such as chloroethyl, their nitrile derivatives, such as $\beta$-cyanethyl, and their alkoxycarbonyl derivatives, such as methoxycarbonylmethyl, ethoxycarbonylmethyl, methoxycarbonylmethyl and ethoxycarbonylethyl.

Cycloalkyl radicals $R_2$ are for example: cyclohexyl.

Aralkyl radicals $R_2$ are for example: benzyl.

Suitable naphtholactams of formula (II) for carrying out the process according to the invention are for example:
N-methyl-naphtholactam-(1,8), N-ethyl-naphtholactam-(1,8), N-iso-propyl-naphtholactam-(1,8), N-n-propyl-naphtholactam-(1,8), N-iso-butyl-naphtholactam-(1,8), N-n-butyl-naphtholactam-(1,8), N-iso-amyl-naphtholactam-(1,8), N-n-hexylnaphtholactam-(1,8), N-cyclohexyl-naphtholactam-(1,8), N-benzyl-naphtholactam (1,8), N-$\beta$-phenylethyl-naphtholactam-(1,8), N-phenyl-naphtholactam-(1,8), and N-2-trimethylene-naphtholactam-(1,8), as well as substituted compounds II, such as N-methoxycarbonylmethyl-naphtholactam-(1,8), N-$\beta$-chloroethylnaphtholactam-(1,8) N-$\beta$-cyanethyl-naphtholactam-(1,8), N-$\beta$-dimethylaminoethyl-naphtholactam-(1,8), N-$\beta$-diethylaminoethylnaphtholactam-(1,8), N-$\beta$-diethylaminoethylnaphtholactam-(1,8), N-$\beta$-piperidinylethyl-naphtholactam-(1,8), N-$\beta$-morpholinylethyl-naphtholactam-(1,8), N-$\beta$-methoxyethylnaphtholactam-(1,8), N-$\beta$-ethoxyethyl-naphtholactam-(1,8), N-$\beta$-methoxycarbonyl-naphtholactam-(1,8) and N-$\beta$-dimethylamidocarbonylethyl-naphtholactam-(1,8), N-methyl-4-chloro-naphtholactam-(1,8), N-ethyl-4-bromo-naphtholactam-(1,8), N-ethyl-4-methoxy-naphtholactam-(1,8), N-n-butyl-4-ethoxy-naphtholactam-(1,8), N-iso-amyl-4-methyl-naphtholactam-(1,8), N-ethyl-4-dimethylamino-naphtholactam-(1,8), N-ethyl-5-chloro-naphtholactam-(1,8), N-methyl-7-methoxy-naphtholactam-(1,8), N-ethyl-4-acetoxy-naphtholactam-(1,8), N-ethyl-4-methylsulphonylaminonaphtholactam-(1,8), N,2- trimethylene-4-chloro-naphthaolactam-(1,8), N-β-cyanethyl-4-bromo-naphtholactam-(1,8), N-β-methoxyethyl-4-methoxy-naphtholactam-(1,8) and N-4'-methoxyphenylnaphtholactam-(1,8).

Suitable amines of formula III are for example: N,N-dimethyl-aniline, N,N-diethyl-aniline, N,N-di-n-propyl-aniline, N,N-di-iso-propyl-aniline, N,N-di-n-butyl-aniline, N,N-di-iso-amyl-aniline, N,N-di-benzyl-aniline, N,N-di-β-chloroethylaniline, N,N-di-β-cyanethyl-aniline and N,N-di-β-ethoxycarbonylethyl-aniline, N-methyl-N-ethyl-aniline, N-ethyl-N-β-chloroethylaniline, N-n-butyl-N-β-cyanethyl-aniline, N-4'-methylphenyl-N-methyl-aniline, N-4'-methoxyphenyl-N-ethyl-aniline, N-4'-chlorophenyl-N-ethyl-aniline, N,N-dimethyl-2-methoxy-aniline, N,N-dimethyl-2-chlor-aniline and N,N-dimethyl-2-ethyl-aniline, N-cyclohexyl-N-methyl-aniline, N,N-di-cyclohexyl-aniline, 1-dimethylamino-naphthalene and 1-diethylamino-naphthalene, and N-ethyl-1,2,3,4-tetrahydroquinoline.

To carry out the process according to the invention an amine of formula III is warmed with the acid halide which serves as the condensation agent, for example phosphorous oxychloride, phosphorus oxybromide, phosphorus tribromide, phosphorus trichloride and thionyl chloride — preferably with phosphorus oxychloride — or with a mixture of such acid halides, phosphorus pentoxide is added, and a naphtholactam derivative of formula II is added at a temperature of between 20° C and 120° C, preferably 60° to 90° C. The end of the reaction can be ascertained according to customary methods, for example by measuring the extinction of the dyestuff formed or through the disappearance of the characteristic fluorescence of the lactam component. It is also possible to follow the inverse procedure by first introducing a mixture of, for example, phosphorus oxychloride with phosphorus pentoxide and the lactam component II, and gradually adding the amine III. This inverse sequence of carrying out the reaction is advantageous if a higher-melting naphtholactam derivative is used. Furthermore, it is also possible to add the phosphorus pentoxide to the mixture of lactam component II, amine III and phosphorus oxychloride.

The use of an inert diluent for performing the condensation is possible, but is generally not necessary; appropriately, such as excess of the acid chloride is used that the latter can at the same time serve as the solvent. The phosphorus pentoxide is added in an amount of 0.2 to 2 mols, relative to 1 mol of naphtholactam derivative. Larger quantities can also be added without the quality of the dyestuff formed suffering; however, the use of approximately equimolar amounts is preferred.

The anion X is unimportant as regards the tinctorial properties of the dyestuffs I; its nature is determined by the acid halide, used as the condensation agent, from which it is formed. In general — since phosphorus oxychloride is preferentially used as the condensation agent — the dyestuffs I are isolated, and used, as chlorides.

In comparison to the process described in German Published Specification 1,190,126, the process according to the invention is distinguished in that it leads to very pure dyestuffs, with significantly improved yields.

The parts quoted in the examples which follow are parts by weight.

EXAMPLE 1

112 parts of phosphorus oxychloride, 42.8 parts of 4-brom-N-ethyl-1,8-naphtholactam and 26 parts of phosphorus pentoxide are warmed to 80° C whilst stirring. 32 parts of N,N-diethyl-aniline are now allowed to run into the mix over the course of about four hours, whilst keeping the temperature at 80° to 90° C. The mixture is stirred for several hours more at this temperature and is then allowed to run into 1,300 parts of water at 40° C. When hydrolysis of the excess condensation agent is complete, the resulting dyestuff solution is adjusted to pH 1.5–2 by adding approx. 160 parts of 50 % strength sodium hydroxide solution, whereupon the dyestuff of formula

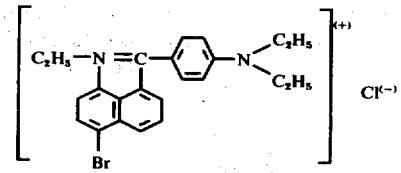

separates out in a crystalline form and in practically quantitative yield. The dyestuff is very pure and yields brilliant, very fast, blue dyeings and prints on polyacrylonitrile fabrics.

If the starting products indicated in the table which follows are used, very fast dyestuffs are again obtained if the same procedure is followed:

Table

| Compound II | Compound III | Colour Shade |
| --- | --- | --- |
| N-Methyl-4-bromo-naphtholactam-(1,8) | N,N-Diethyl-aniline | blue |
| N-n-Propyl-4-bromo-naphtholactam-(1,8) | N,N-Diethyl-aniline | blue |
| N-n-propyl-4-bromo-naphtholactam-(1,8) | N,N-Diethyl-aniline | blue |
| N-Ethyl-2,4-dibromo-naphtholactam-(1,8) | N,N-Diethyl-aniline | blue |
| N-Ethyl-4-chloro-naphtholactam-(1,8) | N,N-Diethyl-aniline | blue |
| N-Ethyl-4-bromo-naphtholactam-(1,8) | N,N-Dimethyl-aniline | reddish-tinged blue |
| N-Ethyl-4-bromo-naphtholactam-(1,8) | N,N-Di-n-propyl-aniline | blue |
| N-Ethyl-4-bromo-naphtholactam-(1,8) | N-Ethyl-N-β-cyanethyl-aniline | reddish-tinged blue |
| N-Ethyl-naphtholactam-(1,8) | N,N-Dimethyl-aniline | violet |
| N-Ethyl-naphtholactam-(1,8) | N,N-Di-β-chlorethyl-aniline | violet |
| N-Ethyl-naphtholactam-(1,8) | N,N-Dimethyl-3-methoxy-aniline | violet |

EXAMPLE 2

68.2 parts of N-methyl-4-ethoxydiphenylamine, 120 parts of phosphorus oxychloride and 40 parts of phosphorus pentoxide are mixed and warmed to 60° C whilst stirring. 59.1 parts of N-ethyl-1,8-naphtholactam are then introduced into the mix over the course of 2 to 3 hours, whilst keeping the temperature at 60° to 70° C. The mixture is stirred for some hours more at 60° to 70° C and is then allowed to run into 2,500 parts of water at 50° C. The excess condensation agent is decomposed and the dyestuff of formula

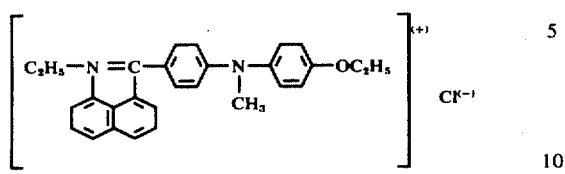

separates out, after cooling, in a crystalline form and in practically quantitative yield. The dyestuff is very pure and yields strongly reddish-tinged blue dyeings and prints of outstanding fastness to light on polyacrylonitrile fabrics.

If the starting products mentioned in the table which follows are used, very fast dyestuffs are again obtained on following the same procedure.

$R_2$ is alkyl of 1–5 atoms; alkyl of 1–5 carbon atoms substituted by a member of the group consisting of chloro, cyano, methoxycarbonyl and ethoxycarbonyl; cyclohexyl; benzyl; or trimethylene to form a ring structure when it is attached to the carbon atom of the phenyl ring adjacent to the carbon atom to which the nitrogen is attached;

X is an anion;

by condensation at a temperature of 20°–120° C. of a naphtholactam derivative of the formula:

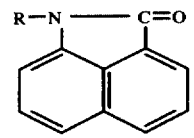

with an aromatic amine of the formula:

Table

| Compound II | Compound III | Colour Shade |
| --- | --- | --- |
| N-Methyl-naphtholactam-(1,8) | 4-Methoxy-N-ethyl-diphenylamine | strongly reddish-tinged blue |
| N-Ethyl-4-bromo-naphtholactam-(1,8) | 4-Methoxy-N-ethyl-diphenylamine | blue |
| N-n-Butyl-4-bromo-naphtholactam-(1,8) | N-Ethyl-diphenylamine | blue |
| N-n-Butyl-4-chloro-naphtholactam-(1,8) | N-Methyl-diphenylamine | blue |
| N-Ethyl-4-dimethylamine-naphtholactam-(1,8) | 4-Ethoxy-N-methyl-diphenylamine | blue-green |
| N,2-Trimethylene-naphtholactam-(1,8) | 4-Ethoxy-N-methyl-diphenylamine | blue-violet |

I claim:

1. Process for the manufacture of cationic dyestuffs of the formula:

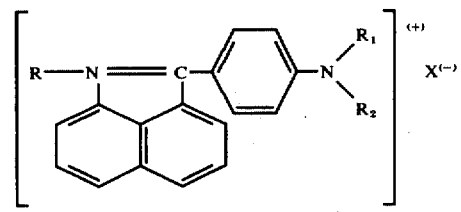

wherein

R is alkyl of 1-6 carbon atoms; alkyl of 1–6 carbon atoms substituted by a member of the group consisting of methoxy, ethoxy, methoxycarbonyl, ethoxycarbonyl, dimethylamidocarbonyl, diethylamidocarbonyl, piperidinyl, morpholinyl, chloro, cyano, dimethylamino and diethylamino; cyclohexyl; benzyl; β-phenylethyl; phenyl; phenyl substituted by methyl or methoxy; or trimethylene to form a ring structure attached to the carbon atom of the naphthalene ring adjacent to the carbon atom to which the nitrogen is attached;

$R_1$ is alkyl of 1–5 carbon atoms; alkyl of 1–5 carbon atoms substituted by a member of the group consisting of chloro, cyano, methoxycarbonyl and ethoxycarbonyl; cyclohexyl; benzyl; phenyl; phenyl substituted by methyl, methoxy, ethoxy or chloro; or trimethylene to form a ring structure when it is attached to the carbon atom of the phenyl ring adjacent to the carbon atom to which the nitrogen is attached;

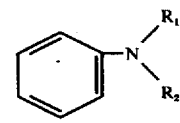

wherein R, $R_1$, and $R_2$ have the above-described meanings, in the presence of an inorganic acid halide condensation agent and phosphorus pentoxide in the amount of 0.2–2 mols of phosphorus pentoxide per mole of said naphtholactam derivative; the ring structures in each of the foregoing formulas being unsubstituted or substituted with one or more non-ionic substituents from the group consisting of chloro, bromo, methyl, ethyl, methoxy, ethoxy, acetoxy, dimethylamino, and methylsulfonylamino, and additionally, the benzene ring in said formulas may be substituted by a fused benzene ring.

2. The process of claim 1 wherein the naphthalene ring structure in said formulas is unsubstituted or substituted by chloro, bromo, methoxy, ethoxy, methyl, dimethylamino, acetoxy, or methylsulfonylamino; and the benzene ring in said formulas is unsubstituted or substituted by methoxy, chloro, ethyl, or fused benzene ring.

3. Process according to claim 1, in which phosphorus oxychloride is used as the acid halide.

4. Process according to claim 1, in which the reaction is carried out in the presence of excess phosphorus oxychloride as the diluent.

5. Process according to claim 1, in which the reaction is carried out at temperatures between 60° and 90° C.

6. Process according to claim 1, in which phosphorus pentoxide is used in approximately equimolar amounts.

* * * * *